United States Patent
Shelton, IV et al.

(10) Patent No.: US 10,646,221 B2
(45) Date of Patent: May 12, 2020

(54) SURGICAL ADJUNCT RETAINING MECHANISMS

(71) Applicant: Ethicon LLC, Guaynabo, PR (US)

(72) Inventors: Frederick E. Shelton, IV, Hillsboro, OH (US); Jason L. Harris, Lebanon, OH (US); Michael J. Vendely, Lebanon, OH (US)

(73) Assignee: Ethicon LLC, Guaynabo, PR (US)

(*) Notice: Subject to any disclaimer, the term of this patent is extended or adjusted under 35 U.S.C. 154(b) by 473 days.

(21) Appl. No.: 15/435,937

(22) Filed: Feb. 17, 2017

(65) Prior Publication Data

US 2018/0235612 A1 Aug. 23, 2018

(51) Int. Cl.
| | | |
|---|---|---|
| A61B 17/03 | (2006.01) | |
| A61B 17/068 | (2006.01) | |
| A61B 17/11 | (2006.01) | |
| A61B 17/072 | (2006.01) | |
| A61B 17/115 | (2006.01) | |

(52) U.S. Cl.
CPC ...... *A61B 17/072* (2013.01); *A61B 17/07207* (2013.01); *A61B 17/07292* (2013.01); *A61B 17/1155* (2013.01); *A61B 2017/07257* (2013.01); *A61B 2017/07271* (2013.01); *A61B 2017/07278* (2013.01)

(58) Field of Classification Search
CPC .... A61B 17/07292; A61B 2017/00004; A61B 2017/0406
See application file for complete search history.

(56) References Cited

U.S. PATENT DOCUMENTS

| | | | |
|---|---|---|---|
| 5,263,629 A * | 11/1993 | Trumbull | A61B 17/07207 128/898 |
| 5,542,594 A | 8/1996 | McKean et al. | |
| 7,143,925 B2 | 12/2006 | Shelton, IV et al. | |
| 7,601,118 B2 | 10/2009 | Smith et al. | |
| 8,028,883 B2 * | 10/2011 | Stopek | A61B 17/072 227/175.1 |
| 8,317,070 B2 | 11/2012 | Hueil et al. | |
| 8,393,514 B2 | 3/2013 | Shelton, IV et al. | |
| 9,055,944 B2 * | 6/2015 | Hodgkinson | A61B 17/07292 |
| 9,282,962 B2 | 3/2016 | Schmid et al. | |
| 9,693,772 B2 * | 7/2017 | Ingmanson | A61B 17/07292 |

(Continued)

FOREIGN PATENT DOCUMENTS

| | | | | |
|---|---|---|---|---|
| EP | 1621141 A2 * | 2/2006 | ....... | A61B 17/07207 |
| EP | 2008595 A2 * | 12/2008 | ....... | A61B 17/07207 |

OTHER PUBLICATIONS

Ethicon Endo-Surgery, Inc. (2015) Echelon Flex: Engineering a Better Grip on Movement. [Brochure].

*Primary Examiner* — Andrew M Tecco
*Assistant Examiner* — Eyamindae C Jallow
(74) *Attorney, Agent, or Firm* — Mintz Levin Cohn Ferris Glovsky and Popeo, P.C.

(57) ABSTRACT

An adjunct can be releasably retained on an end effector of a surgical tool, such as a surgical stapler, using a plurality of retaining elements. The retaining elements can be configured to retain the adjunct to the end effector with a mechanical force until a force is applied to the adjunct that overcomes the mechanical force, thereby allowing release of the adjunct from the end effector and into a patient's body.

20 Claims, 12 Drawing Sheets

(56) References Cited

U.S. PATENT DOCUMENTS

| | | | |
|---|---|---|---|
| 2002/0165559 A1* | 11/2002 | Grant et al. | A61B 17/07207 606/139 |
| 2009/0206126 A1 | 8/2009 | Huitema et al. | |
| 2012/0080336 A1 | 4/2012 | Shelton, IV et al. | |
| 2013/0221065 A1 | 8/2013 | Aronhalt et al. | |
| 2013/0256377 A1 | 10/2013 | Schmid et al. | |
| 2014/0151431 A1 | 6/2014 | Hodgkinson et al. | |
| 2014/0166721 A1 | 6/2014 | Stevenson et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1* | 5/2015 | Shelton, IV | A61B 17/07292 623/23.72 |
| 2015/0134077 A1 | 5/2015 | Shelton, IV et al. | |
| 2015/0272575 A1 | 10/2015 | Leimbach et al. | |
| 2015/0277471 A1 | 10/2015 | Leimbach et al. | |
| 2015/0351758 A1 | 12/2015 | Shelton, IV et al. | |
| 2016/0089142 A1 | 3/2016 | Harris et al. | |
| 2017/0055986 A1 | 3/2017 | Harris et al. | |

* cited by examiner

SURGICAL ADJUNCT RETAINING MECHANISMS

FIELD

The present disclosure relates generally to surgical adjunct retaining mechanisms.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

In general, surgical adjunct retaining mechanisms are provided.

In one aspect, a staple cartridge assembly for use with a surgical stapler is provided that in one embodiment includes a cartridge body having a plurality of staple cavities on a tissue-facing surface thereof, and a tray having the cartridge body seated therein. Each staple cavity has a surgical staple disposed therein. The tray includes a plurality of retaining elements on opposed longitudinal sides of the tray extending along opposed longitudinal sides of the cartridge body. The plurality of retaining elements are configured to releasably engage a biocompatible adjunct material such that the adjunct material is disposed on the tissue-facing surface of the cartridge body and is configured to be delivered to tissue by deployment of the surgical staples from the cartridge body and thereby be released from the plurality of retaining elements.

The staple cartridge can vary in any number of ways. For example, the plurality of retaining elements can include hooks that are each angled in a same direction.

For another example, the plurality of retaining elements can include linear pegs extending in a direction substantially perpendicular to the opposed longitudinal sides of the cartridge body. In at least some embodiments, each of the linear pegs can include a gripping feature thereon configured to facilitate gripping of the adjunct material.

For yet another example, the tray and the cartridge body can be in a fixed position relative to one another. For another example, the tray can be configured to slide longitudinally relative to the cartridge body and thereby allow the release of the adjunct material from the plurality of retaining elements. For still another example, the tray having the cartridge body seated therein can be configured to be releasably seated in a jaw of a surgical stapler. For yet another example, the adjunct material can be made of a plurality of fibers. For another example, the adjunct material can be a film, and each of the plurality of retaining elements can pierce the film.

In another aspect, an end effector for a surgical instrument is provided that in one embodiment includes a first jaw having a cartridge body removably attached thereto, a second jaw having an anvil with a plurality of staple forming cavities formed on a tissue-facing surface thereof, and a retainer at one of the first and second jaws. The cartridge body can have a plurality of staple cavities configured to seat staples therein that are configured to be deployed from the staple cavities into tissue. The first and second jaws are configured to clamp the tissue therebetween. The retainer has a plurality of extensions extending therefrom in a direction toward the other one of the first and second jaws. The plurality of extensions are configured to engage a biocompatible adjunct material to releasably retain the adjunct material to the one of the first and second jaws. The deployment of the staples is configured to cause the staples to pierce the adjunct material and to cause the adjunct material to be released from the plurality of retaining elements.

The end effector can have any number of variations. For example, the plurality of extensions can be arranged longitudinally along each of opposed longitudinal sides of the one of the first and second jaws. For another example, the plurality of extensions can include one of a plurality of hooks and a plurality of linear pegs. For yet another example, the adjunct material can be made of a plurality of fibers. For another example, the adjunct material can be a film, and each of the plurality of extensions can pierce the film.

For yet another example, the one of the first and second jaws can be the first jaw, and the other one of the first and second jaws can be the second jaw. In at least some embodiments, the retainer can be a tray seating the cartridge body therein, and the tray can be seated in a channel of the first jaw.

For still another example, the one of the first and second jaws can be the second jaw, and the other one of the first and second jaws can be the first jaw. In at least some embodiments, the retainer is releasably coupled to the anvil.

In another aspect, a surgical method is provided that in one embodiment includes advancing a surgical stapler into a body of a patient. The surgical stapler has a pair of jaws at a distal end thereof. One of the jaws has a retainer releasably coupled thereto. The retainer has a plurality of retaining elements extending therefrom toward the other of the jaws. Each of the plurality of retaining elements engage an adjunct material to retain the adjunct material to the one of the jaws with a mechanical retention force. The surgical method also includes engaging tissue with the pair of jaws, and actuating the surgical stapler that is engaging the tissue. The actuating causes a plurality of staples to pierce the adjunct material and be ejected from the surgical stapler into the tissue. The ejection of the staples overcomes the mechanical retention force so as to cause release of the adjunct material from the one of the jaws.

The surgical method can vary in any number of ways. For example, engaging the tissue can include clamping the tissue between tissue-facing surfaces of the pair of jaws. For another example, the plurality of retaining elements can include one of a plurality of hooks and a plurality of linear pegs. For yet another example, each of the plurality of retaining elements can engage fibers of the adjunct material. For still another example, the adjunct material can be a film, and each of the plurality of retaining elements can pierce the film.

BRIEF DESCRIPTION OF DRAWINGS

This invention will be more fully understood from the following detailed description taken in conjunction with the accompanying drawings, in which.

DETAILED DESCRIPTION

Figure 1:
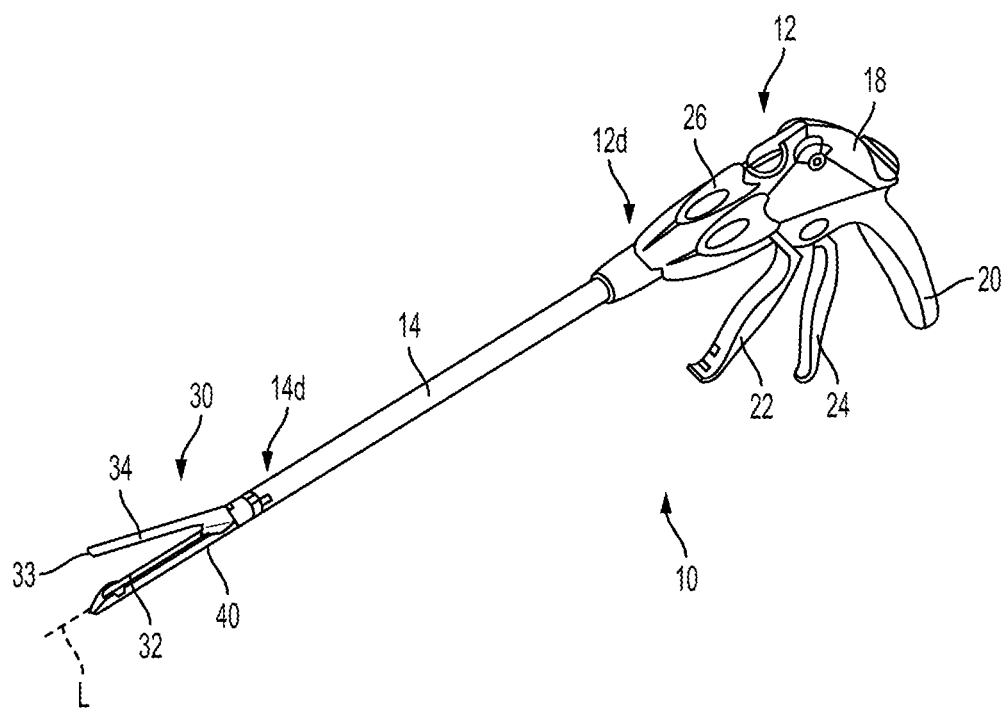
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used on a variety of tissues in a variety of different surgical procedures, for example in thoracic surgery or in gastric surgery.

Figure 2:
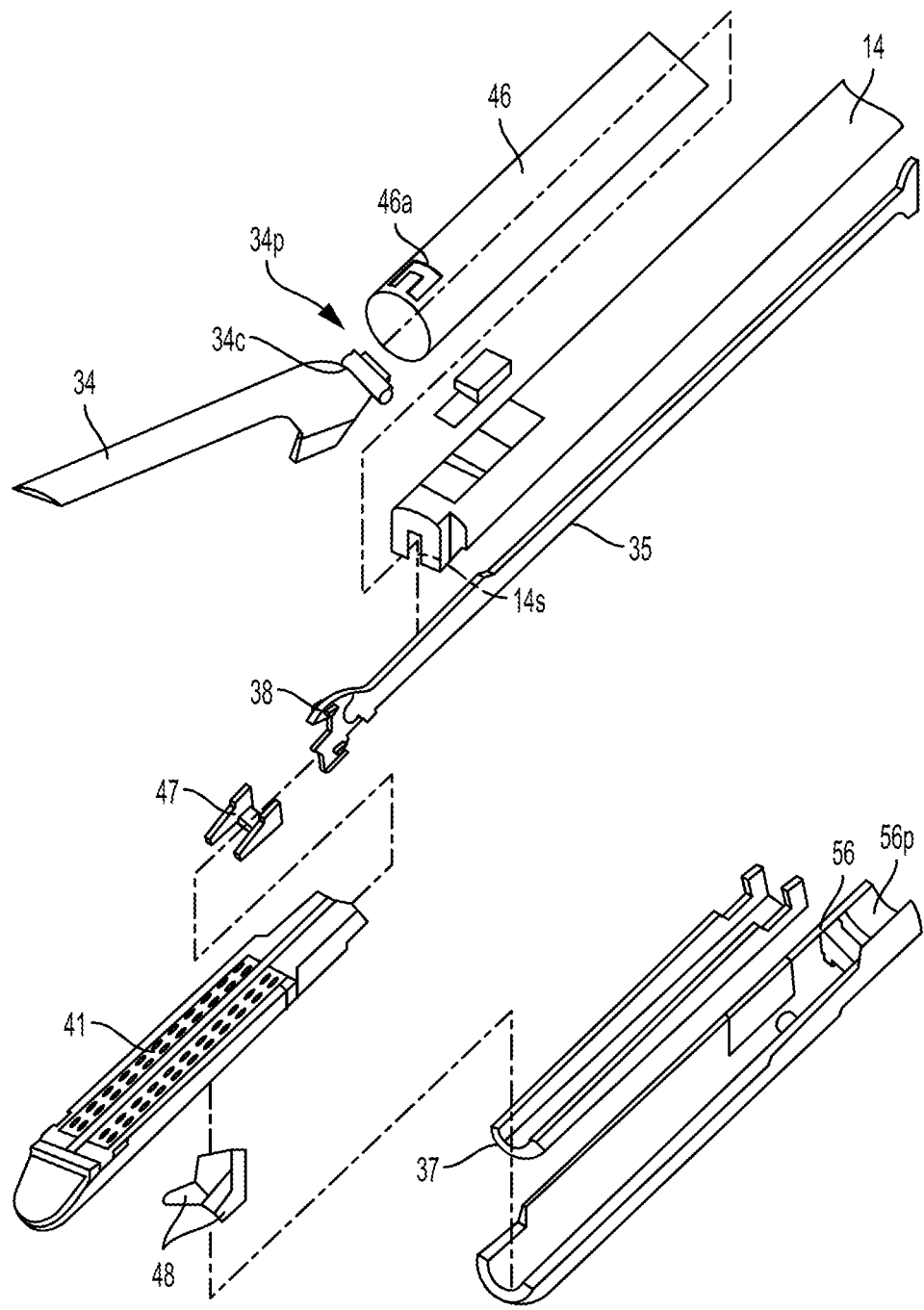
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
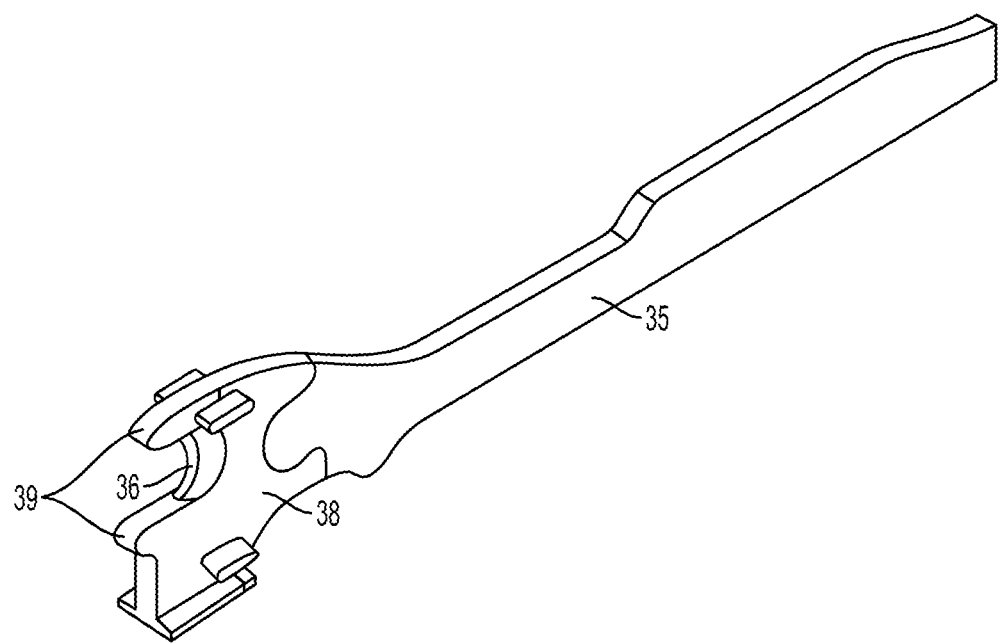
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
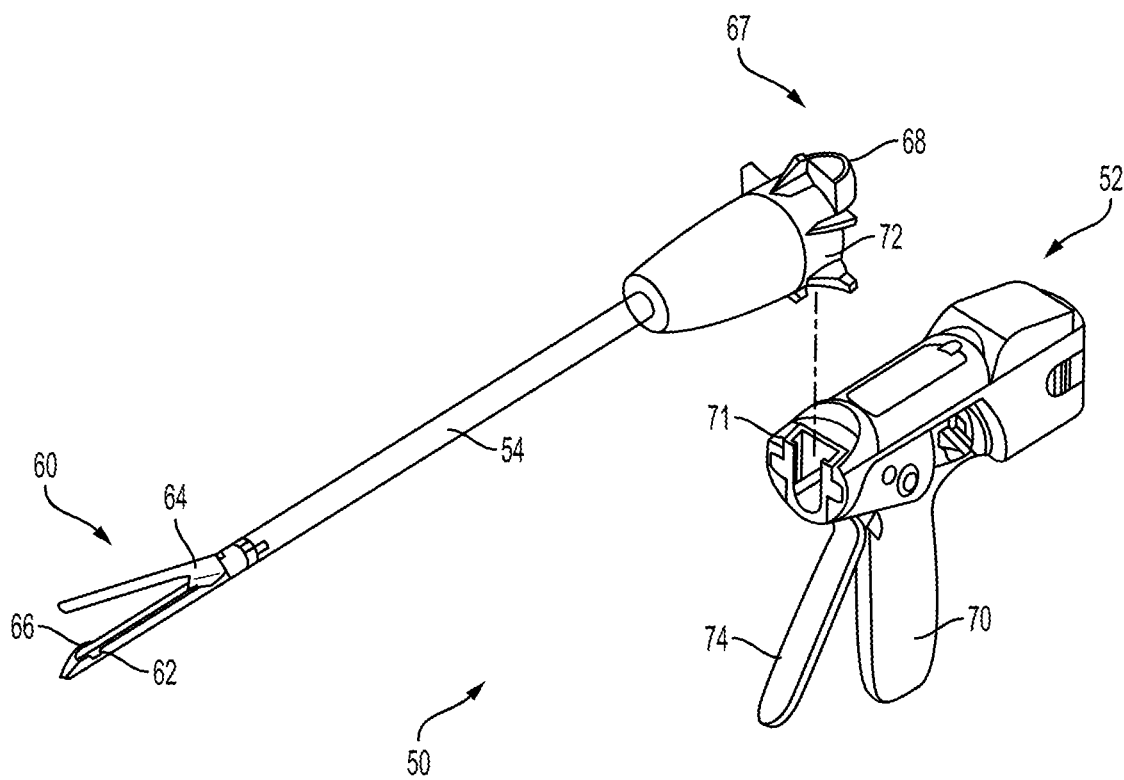
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
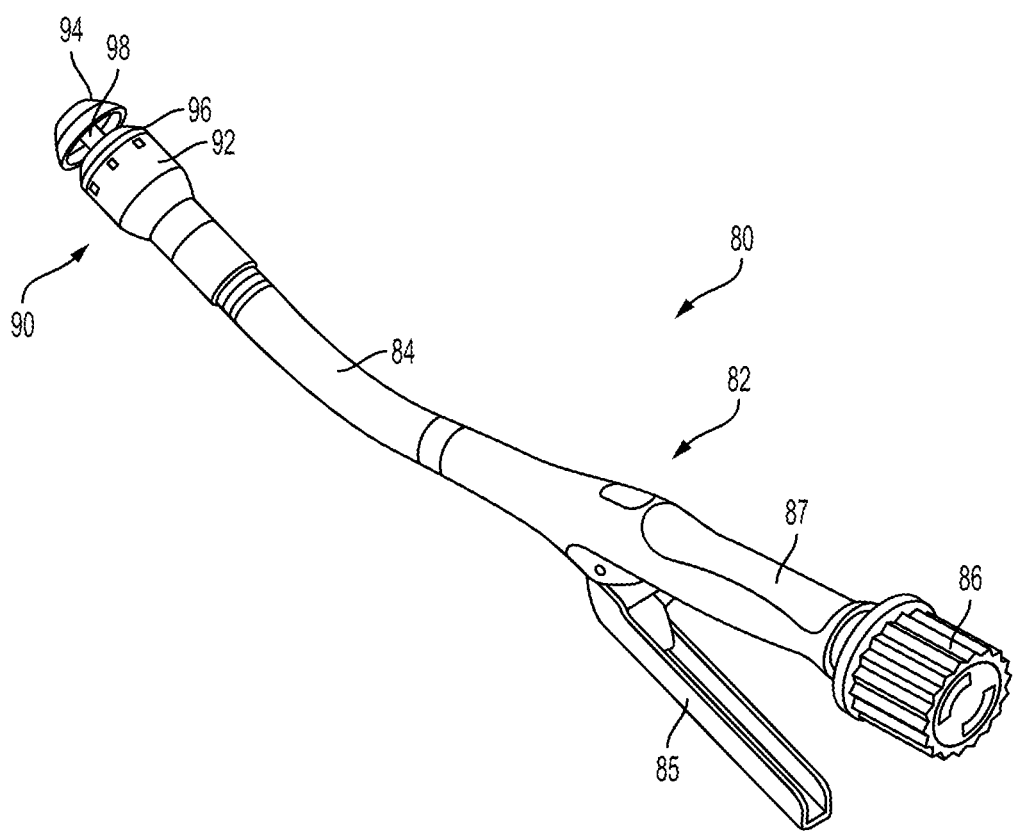
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Implementations

An adjunct can be releasably retained on an end effector of a surgical tool, such as a surgical stapler, using a plurality of retaining elements. The retaining elements can be configured to retain the adjunct to the end effector with a mechanical force until a force is applied to the adjunct that overcomes the mechanical force, thereby allowing release of the adjunct from the end effector and into a patient's body where it may provide any number of benefits, as discussed above. The force can be applied to the adjunct in the normal course of use of the surgical tool, such as in the course of deploying staples from the end effector, which may facilitate ease of use since a user need not take any special action to release the adjunct. The retaining elements can be configured to releasably retain the adjunct to the end effector without using an adhesive, which may make the system easier to assemble, may facilitate release of the adjunct from the end effector since adhesive may require application of a higher force to release an adjunct, and/or may prevent staple cavities or other components of a surgical tool from being clogged by or otherwise compromised in function by the adhesive. The retaining elements can be on a retainer releasably coupled to the end effector. Existing end effectors may be retrofitted with a retainer and/or existing staple cartridges may be coupled to the retainer. Existing end effectors that include a metal pan may have the pan modified to include the features of a retainer as described herein.

Figure 6:
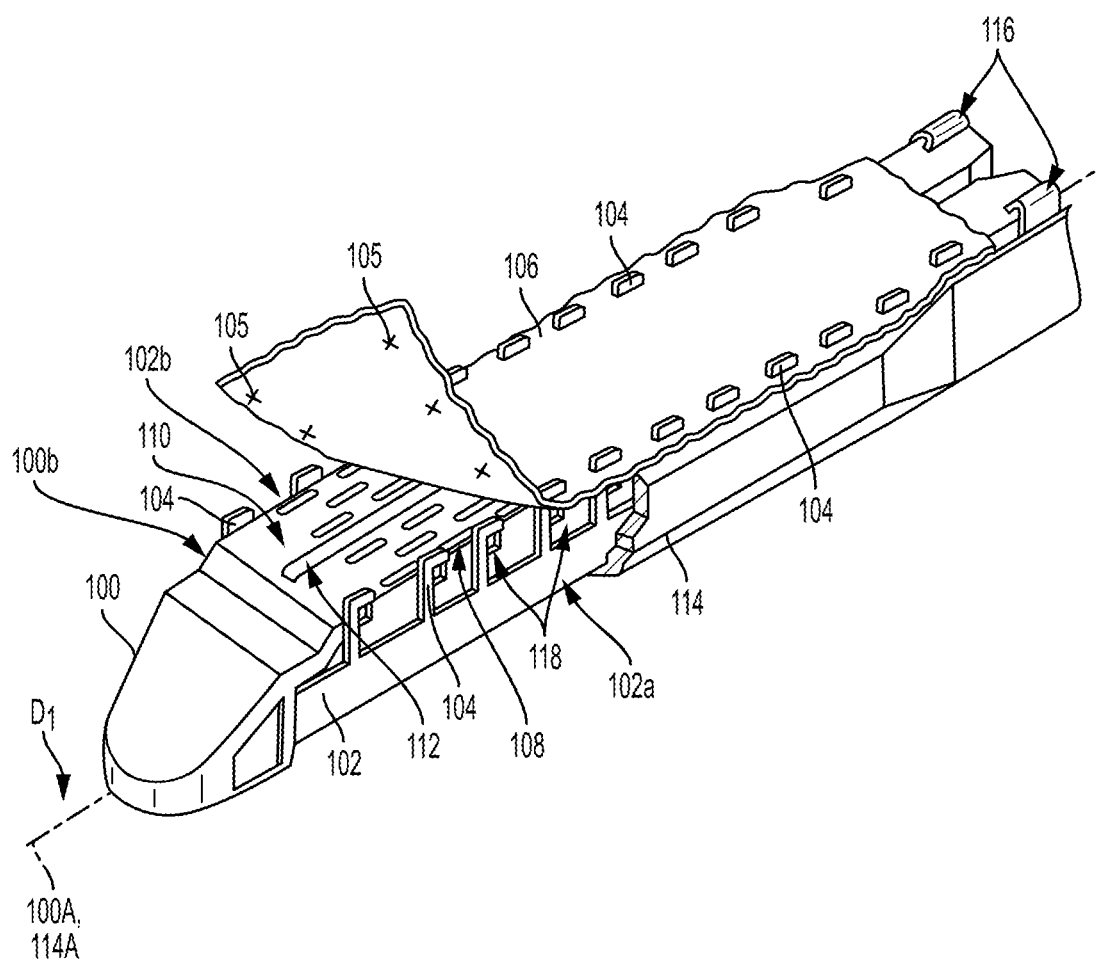
FIG. 6 is a perspective, partial cutaway view of one embodiment of a cartridge having an adjunct releasably retained thereon via a retainer.

FIG. 6 illustrates one embodiment of a staple cartridge 100 coupled to a retainer 102 including a plurality of retaining elements 104 configured to releasably retain an adjunct 106 to the staple cartridge 100. The staple cartridge 100 is generally configured and used similar to the staple cartridge 40 of FIGS. 1 and 2, e.g., has a plurality of staple cavities 108 in a tissue-facing surface 110 thereof that each seat a staple therein (the staples are obscured in FIG. 6), is configured to have a sled moved therethrough to push the staples out of the staple cavities 108, has a longitudinal slot 112 through which a knife or other cutting element can translate to cut tissue, etc. The staple cartridge 100 is releasably seated in a lower jaw 114 of an end effector of a surgical tool. The cartridge 100 is seated in the retainer 102, which is seated in a channel in the lower jaw 114. The sled that translates along the cartridge 100 can thus translate along an inner bottom surface of the retainer 102. The lower jaw 114 includes a coupling mechanism 116 that couples the lower jaw 114 to an upper jaw of the end effector that is configured to cooperate with the lower jaw 114 to engage and staple tissue, as discussed above.

Figure 7:
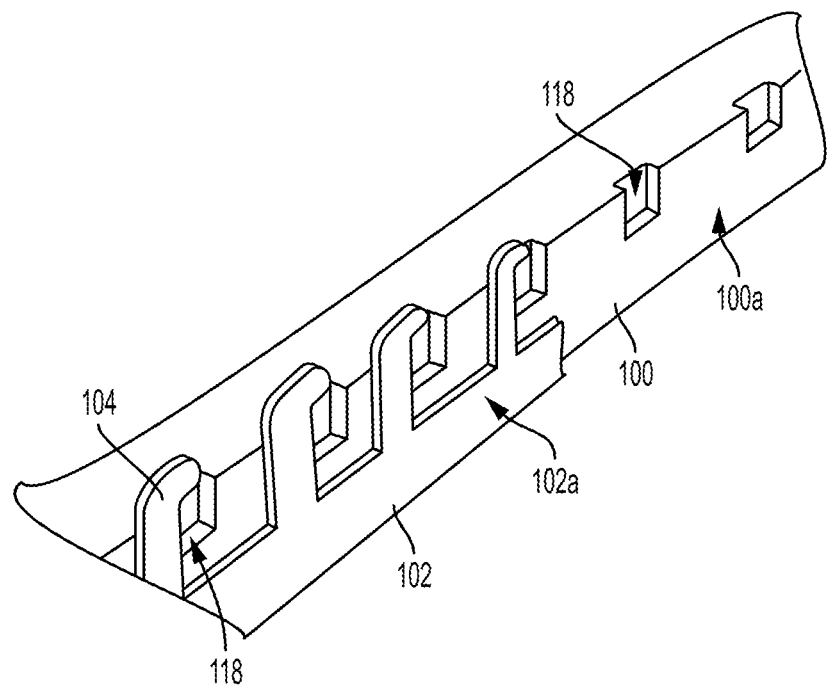
FIG. 7 is a perspective, partial cutaway view of a portion of the cartridge and retainer of FIG. 6.

The retainer 102 in this illustrated embodiment is in the form of a pan or tray that has a bottom with opposed sidewalls extending upwardly therefrom. The cartridge 100 is fixedly seated in the retainer 102 in this illustrated embodiment, e.g., is not removable from the retainer 102. The cartridge 100 and the retainer 102 are thus configured to be removably and replaceably seated in the lower jaw 114 as a unit. The cartridge 100 being fixed to the retainer 102 may help ensure that the retaining elements 104 are in a desirable location relative to the cartridge 100, which may help the adjunct 102 be desirably positioned over the cartridge's tissue-facing surface 110 and/or may help ensure alignment of the retaining elements 104 with cut-outs or pockets 118 formed in the cartridge 100, which are also shown in FIG. 7 and are discussed further below. In other embodiments, a cartridge can be releasably retained in a retainer, which may allow for re-use of the retainer with different staple cartridges. The retainer in such embodiments is configured to be seated in an end effector's lower jaw either before or after the cartridge is seated in the retainer.

The retainer 102 can be formed from any of a variety of materials. In an exemplary embodiment, the retainer 102 is formed from a metal, such as stainless steel, titanium, or a shape memory metal such as Nitinol.

The retaining elements 104 are longitudinally aligned and are positioned along opposed longitudinal sides 102a, 102b of the retainer 102. The retaining elements 104 are thus positioned along opposed longitudinal sides 100a, 100b of the cartridge 100. In an exemplary embodiments, a first number of the retaining elements 104 are on one side 102a (e.g., left side) of the retainer 102 and a second number of the retaining elements 104 are on the other side 102b (e.g., right side) of the retainer 102. The first and second numbers of the retaining elements 104 can be equal, as in this illustrated embodiment in which there are eleven retaining element 104 on each side 102a, 102b of the retainer 102 for a total or twenty-two retaining elements 104. Having an equal number of retaining elements 104 on opposed sides 102a, 102b of the retainer 102 may help provide even securing of the adjunct 106 to the cartridge 100. However, the first and second numbers of the retaining elements 104 can vary. In an exemplary embodiment there are at least three retaining elements 104 on each side 102a, 102b of the retainer 102. For example, one retaining element 104 can be near a proximal end thereof for releasable attachment to the adjunct 100 near a proximal end thereof, one retaining element 104 can be near a distal end thereof for releasable attachment to the adjunct 100 near a distal end thereof, and one retaining element 104 can be near a middle thereof for releasable attachment to the adjunct 100 near a middle thereof. Any additional retaining elements 104 can be located between the proximal retaining element and the middle retaining element and/or between the distal retaining element and the middle retaining element. Regardless of a number of retaining elements 104 on each side 102a, 102b of the retainer 102, the retaining elements 104 can be equidistantly spaced therealong, as in this illustrated embodiment, which may help evenly secure the adjunct 106 to the cartridge 100.

The retaining elements 104 extend upwardly from the retainer 102, e.g., in a direction toward the upper jaw (e.g., the anvil) coupled to the lower jaw 114. The retaining elements 104 thus extend in a direction D1 substantially perpendicular to a longitudinal axis 100A of the cartridge 100 and a longitudinal axis 114A of the lower jaw 114. The retaining elements 104 extending upwardly may help prevent lateral movement of the adjunct 106 engaged therewith relative to the cartridge 100, which may help ensure that all of the staples in the cartridge 100 are deployed through the adjunct 106, e.g., that each of the staples pierces the adjunct 106, which may facilitate release the adjunct 106 from the retaining elements 104 and the cartridge 100. The retaining elements 104 each extend a distance above the tissue-facing surface 110 of the cartridge 100, which allows the adjunct 106 engaged by the retaining elements 104 to be seated on and be substantially flat on the tissue-facing surface 110 of the cartridge 100. A person skilled in the art will appreciate that although the adjunct 106 may not be precisely flat it can nevertheless be considered to be substantially flat due to any number of factors, such as flexibility of the adjunct material and/or manufacturing tolerance at the adjunct's surface.

Each of the retaining elements 104 in this illustrated embodiment is in the form of a hook. Each of the hooks is angled or oriented in a same proximal direction. The hooks are thus angled or oriented in a direction that is opposite to the distal direction that the sled translates along the cartridge 100 and lower jaw 114. As the sled translates distally along the cartridge 100 and lower jaw 114 to eject the staples, the upward movement of the staples out of the staple cavities 108 exerts a force, e.g., an upward force in a direction of the upper jaw against which the staples are pushed, on the adjunct 106. The adjunct 106 is thus urged upwardly away from the cartridge 100, which causes the adjunct 106 to be released from the retaining elements 104 by being pushed thereoff. The retaining elements 104 can experience deformation during the release of the adjunct 106 therefrom in response to the upward force. In other words, the pushing of the adjunct 106 off the retaining elements 104 may cause the hooks to bend upwardly. The force exerted by the staples being ejected through the adjunct 106 can thus be enough to overcome the mechanical force that the retaining elements 104 exert to hold the adjunct 106 thereto. In other embodiments, retaining elements in the form of hooks can each be angled or oriented in a same distal direction so as to be angled in the same direction that the sled translates along the cartridge and lower jaw. In this way, the sled's distal movement can help urge disengagement of the adjunct from the retaining elements as the sled travels in a distal direction to drive staples from the cartridge. The hooks in such an embodiment would be less likely to experience plastic deformation than hooks oriented proximally and may not deform at all.

The retaining elements 104 on the retainer 102 can be integrally formed with the retainer 102, as in this illustrated embodiment, such as with a stamping process. The retaining elements 104 can thus also, in an exemplary embodiment, be formed from a metal. The retaining elements 104 can be very thin, as in this illustrated embodiment, in which case the retaining elements 104 will have some degree of flexibility even if formed from a rigid material such as metal. This flexibility can result in plastic deformation of the retaining elements 104 during release of the adjunct 106 therefrom, e.g., one or more of the retaining elements 104 may be irreversibly bent during release of the adjunct 106, such as by being bent upwardly during staple deployment as discussed above. In other embodiments, instead of being integral with the retainer 102, the retaining elements 104 can be separate members attached thereto, such as by welding, adhesive, press fit, etc.

In at least some embodiments, one or more of the retaining elements 104 can include a gripping feature thereon configured to facilitate gripping of the adjunct 106. The gripping feature may help prevent premature release of the adjunct 106 from the cartridge 100. For example, the gripping feature can be a textured surface on the retaining element 104 that increases friction between the retaining element 104 and the adjunct 106. For another example, the gripping feature can be an enlarged tip of the retaining element 104, such as a bulb or ball at the retaining element's tip, which may help prevent the adjunct 106 from prematurely sliding off the retaining element 104 since passing over the enlarged tip will be made more difficult, e.g., require a higher force to be released therefrom.

The cartridge 100 has a plurality of cut-outs or pockets 118 formed therein. The cut-outs 118 are longitudinally aligned and are positioned along the opposed longitudinal sides 100*a*, 100*b* of the cartridge 100. The cut-outs 118 are aligned with the retaining elements 114 such that each of the cut-outs 118 has an associated retaining element 114. The cut-outs 118 are each configured to seat a portion of the adjunct 106 therein, as shown in FIG. 6, when the retaining elements 104 are holding the adjunct 106 on the cartridge 100. The cut-outs 118 may thus help prevent buckling of the adjunct 106, which may allow the staples to more evenly advance through the adjunct 106. The cut-outs 118 each have a square shape in this illustrated embodiment but can have other shapes, e.g., rectangular, semi-circular, etc.

Figure 8:
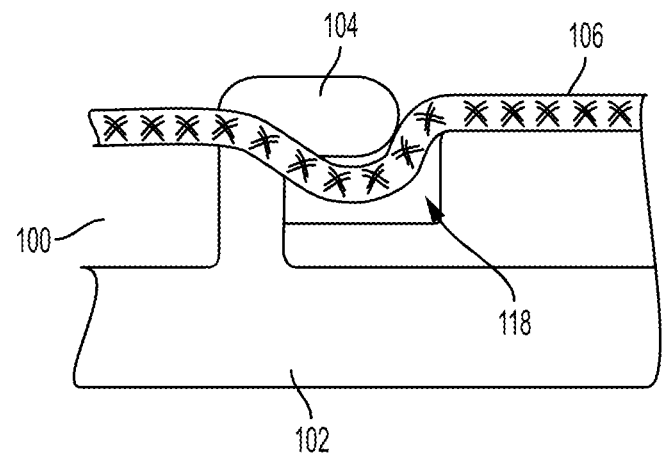
FIG. 8 is a side view of a portion of the cartridge, retainer, and adjunct of FIG. 6.

The adjunct 106 in this illustrated embodiment is a fibrous structure that includes a plurality of fibers. As shown in FIGS. 6 and 8, the retaining elements 104 can extend through the adjunct 106 so as to hook the adjunct 106 thereto. The fibers can separate to allow the retaining elements 104 to extend therethrough at points 105 where the adjunct 106 engages the retaining elements 104, although depending on various factors such as the tightness of the fiber's lattice structure, whether the retaining element's tips are blunted or pointed (the tips are blunted in this illustrated embodiment), and the strength of the retaining elements 104, the retaining elements 104 can pierce through the fibrous structure so as to form holes therein at any one or more of the points 105. The retaining elements 104 pierce through the adjunct 106 in this illustrated embodiment. The adjunct 106 may have pre-formed holes therein at locations where the retaining elements 104 will extend through the adjunct 106, which may help the retaining elements 104 all pass through the adjunct 106 both during loading of the adjunct 106 onto the retaining elements 104 and during release of the adjunct 106 from the retaining elements 104.

In some embodiments, the adjunct 106 can be releasably coupled to the retaining elements 104 in manufacturing such that the cartridge 100, retainer 102, and adjunct 106 can be provided to a user as an assembled unit. Providing such an assembled unit may save user time since the assembly is pre-performed and/or may help ensure that the adjunct 106 is properly secured to the cartridge 100 and retainer 102. In other embodiments, the adjunct 106 can be provided to a user as a separate element from the retainer 102 and cartridge 100, which as mentioned above may be separate elements or may be fixed together as a unit. The adjunct 106 in such embodiments can thus be configured to be coupled to the retainer 102 and cartridge 100 by a user. The adjunct 106 can be coupled to the retainer 102 and cartridge 100 in any of a variety of ways. For example, the adjunct 106 can be manually engaged with the retaining elements 104 by being pressed or slid thereon by hand. For another example, an applicator tool can be configured to have the adjunct 106 loaded thereon, and the applicator tool can be configured to engage the adjunct 106 with the retaining elements 104 by sliding or pressing the adjunct 106 thereon. Use of the applicator tool may allow for more predictable engagement of the adjunct 106 with the retaining elements 104 than application by hand.

Figure 9:
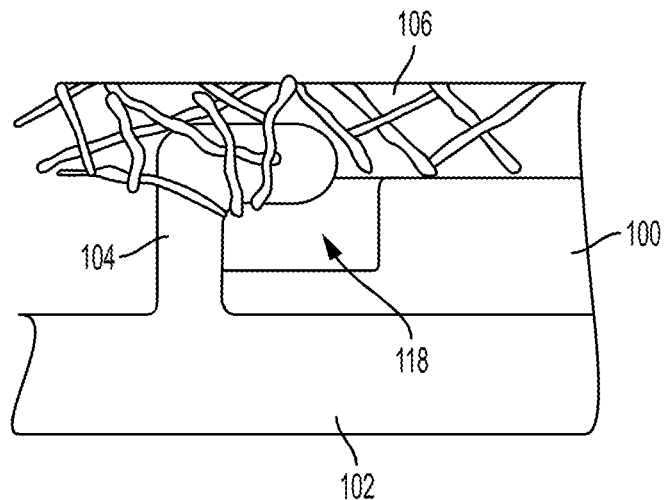
FIG. 9 is another side view of a portion of the cartridge, retainer, and adjunct of FIG. 6.

FIG. 9 illustrates another embodiment of the retaining elements 104 engaging the adjunct 106. In this illustrated embodiment, the retaining elements 104 catch various ones of interlaced fibers of the adjunct 106 to hold the adjunct 106 thereto. Some or all of the retaining elements 104 may therefore not extend above the adjunct 106, as with the retaining element 104 illustrated in FIG. 9.

In other embodiments, the adjunct releasably engaged with the retaining elements 104 can have a configuration other than a fibrous structure. For example, the adjunct can be a film, and the retaining elements 104 can extend through the film so as to hook the adjunct thereto. The film may have pre-formed holes therein at locations where the retaining elements 104 will extend therethrough.

Figure 10:
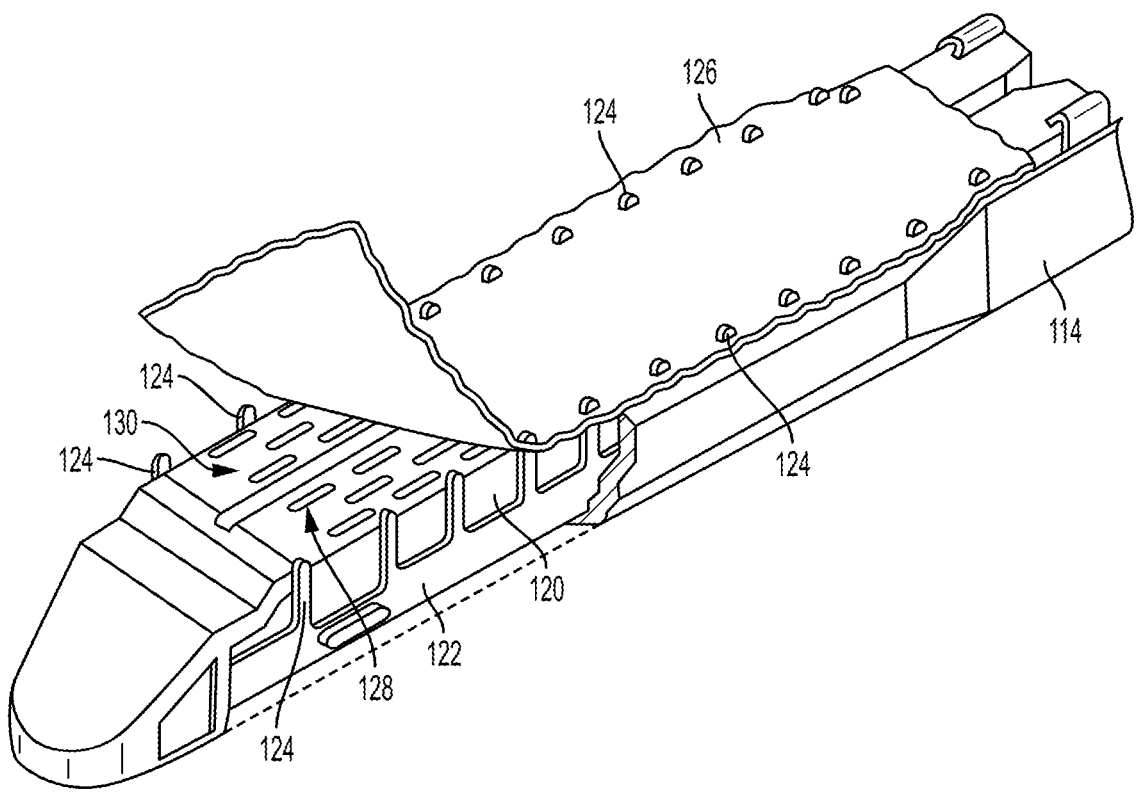
FIG. 10 is a perspective, partial cutaway view of another embodiment of a cartridge having an adjunct releasably retained thereon via a retainer.

FIG. 10 illustrates another embodiment of a staple cartridge 120 coupled to a retainer 122 including a plurality of retaining elements 124 configured to releasably retain an adjunct 126 to the staple cartridge 120. The staple cartridge 120 is generally configured and used similar to the staple cartridge 40 of FIGS. 1 and 2, e.g., has a plurality of staple cavities 128 in a tissue-facing surface 130 thereof that each seat a staple therein (the staples are obscured in FIG. 10), is configured to have a sled moved therethrough to push the staples out of the staple cavities 128, has a longitudinal slot 122 through which a knife or other cutting element can translate to cut tissue, etc. The staple cartridge 120 is releasably seated in the lower jaw 114 of FIG. 6 but can be similarly seated in other types of jaws. The cartridge 120 in this illustrated embodiment does not have any cut-outs or pockets formed therein, but in other embodiments may have a plurality of cuts-outs similar to the cut-outs 118 of the cartridge 100 of FIG. 6. The adjunct 126 is a fibrous structure similar to the adjunct 106 of FIG. 6 but can have other configurations.

The retainer 122 is generally configured and used similar to the retainer 102 of FIG. 6. The retainer 122 in this illustrated embodiment is in the form of a pan or tray that has a bottom with opposed sidewalls extending upwardly therefrom. The cartridge 120 is fixedly seated in the retainer 122, which is seated in a channel in the lower jaw 114, but can instead be releasably seated in the retainer 122.

The retaining elements 124 are also generally configured and used similar to the retaining elements 114 of FIG. 6, e.g., are longitudinally aligned along opposed sides of the retainer 122 and along opposed sides of the cartridge 120, extend upwardly toward the upper jaw coupled to the lower jaw 114, etc. However, in this illustrated embodiment, the retaining elements 124 are in the form of pegs that extend upwardly from the retainer 122. The adjunct 126 is configured to be coupled with the retaining elements 124 by being pushed straight down thereon, such as by hand or with an applicator tool. Such loading may be easier than with retaining elements in the form of hooks, since an adjunct may need to be loaded onto hooks at an angle that may generally be less intuitive than a straight down motion. The retaining elements 124 are integrally formed with the retainer 122, but similar to that discussed above, can be otherwise attached thereto. In at least some embodiments, one or more of the retaining elements 124 can include a gripping feature thereon configured to facilitate gripping of the adjunct 126, similar to that discussed above.

Figure 11:
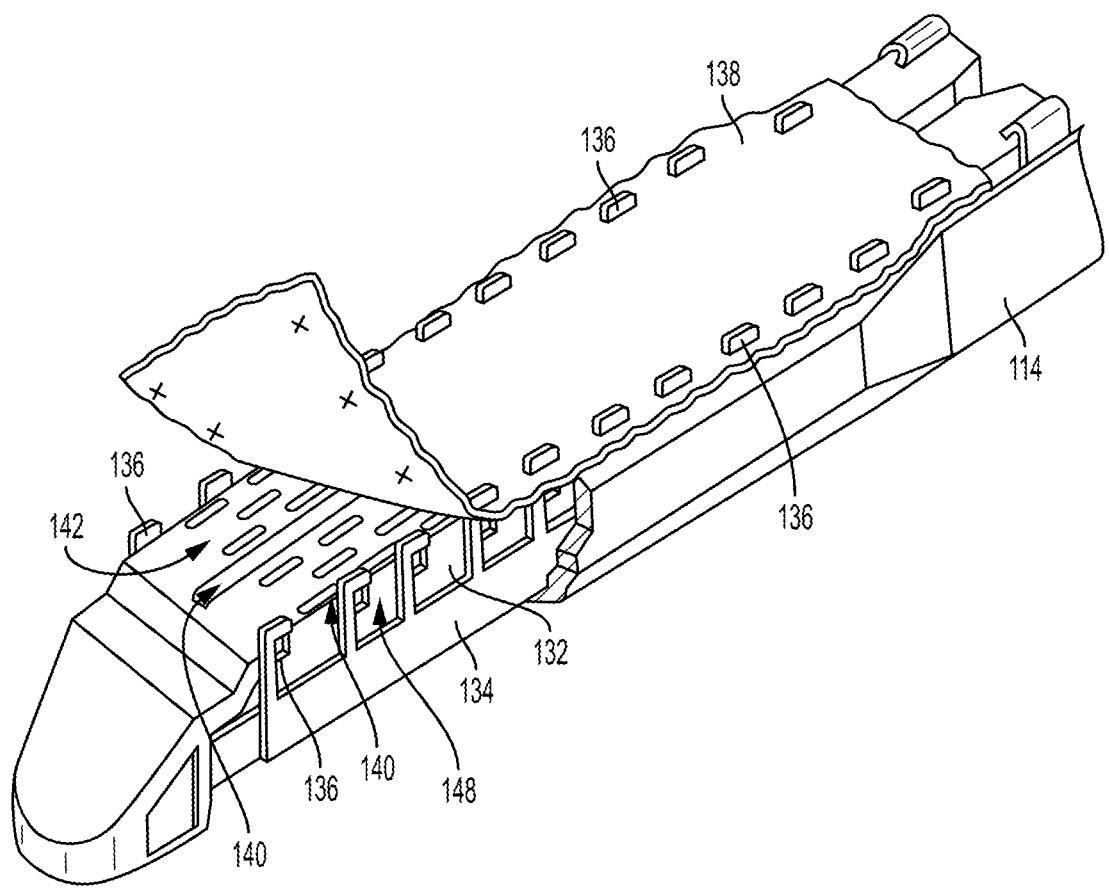
FIG. 11 is a perspective, partial cutaway view of yet another embodiment of a cartridge having an adjunct releasably retained thereon via a retainer.
Figure 12:
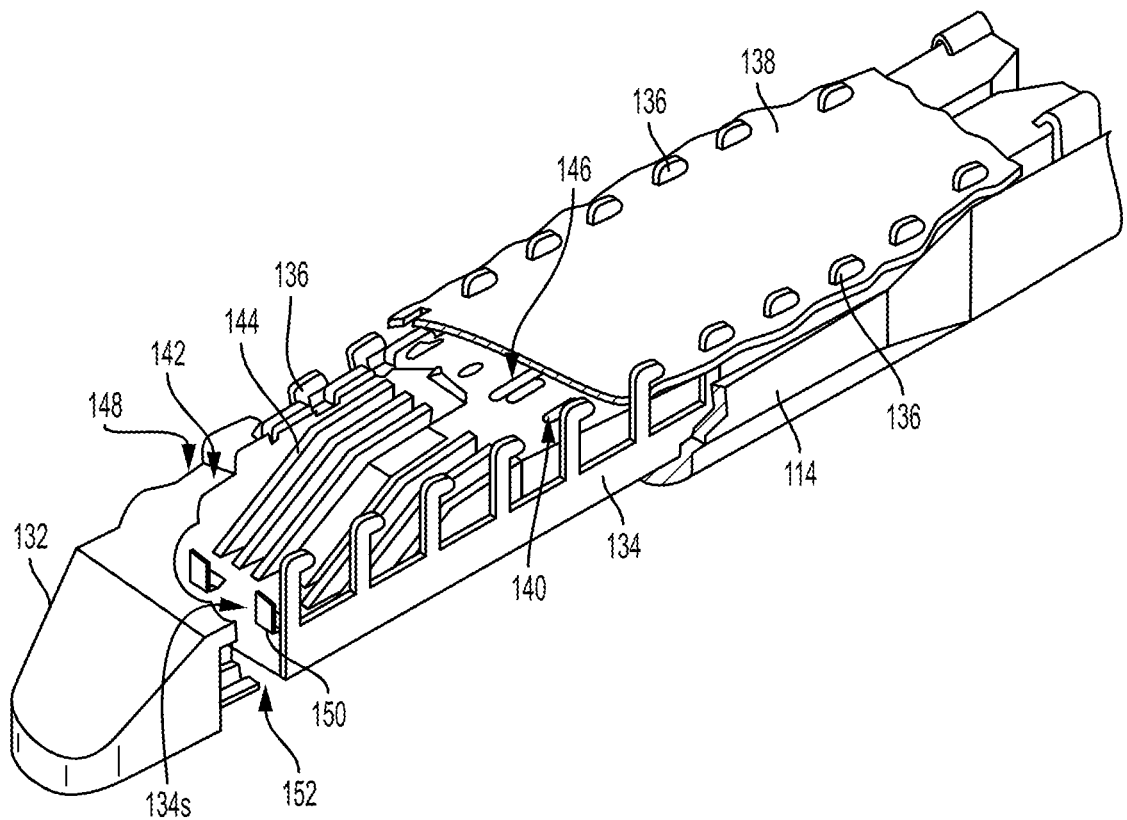
FIG. 12 is another perspective, partial cutaway view of the cartridge, retainer, and adjunct of FIG. 11.

FIGS. 11 and 12 illustrate another embodiment of a staple cartridge 132 coupled to a retainer 134 including a plurality of retaining elements 136 configured to releasably retain an adjunct 138 to the staple cartridge 132. The staple cartridge 132 is generally configured and used similar to the staple cartridge 40 of FIGS. 1 and 2, e.g., has a plurality of staple cavities 140 in a tissue-facing surface 142 thereof that each seat a staple therein (the staples are obscured in FIG. 11 and have already been deployed in FIG. 12), is configured to have a sled 144 moved therethrough to push the staples out of the staple cavities 140, has a longitudinal slot 146 through which a knife or other cutting element can translate to cut tissue, etc. The sled 144 is shown in a distal position in FIG. 12 after it has slid distally a partial distance along an inner bottom surface 134s of the retainer 134 to deploy staples from the cartridge 132, prior to release of the adjunct 138, which is discussed further below. The adjunct 138 is a fibrous structure similar to the adjunct 106 of FIG. 6 but can have other configurations. The retaining elements 136 are also generally configured and used similar to the retaining elements 114 of FIG. 6, e.g., are longitudinally aligned along opposed sides of the retainer 134 and along opposed sides of the cartridge 132, extend upwardly toward the upper jaw coupled to the lower jaw 114, are in the form of hooks angled proximally, etc.

Figure 13:
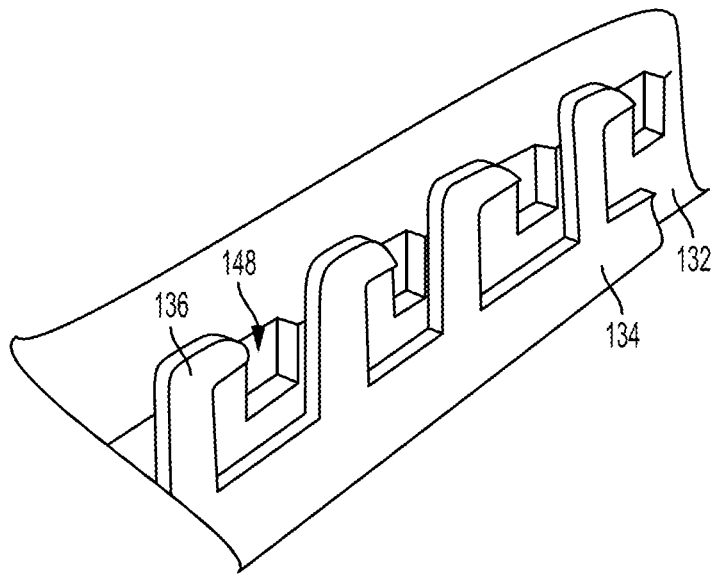
FIG. 13 is a side view of a portion of the cartridge and retainer of FIG. 11.

The staple cartridge 132 is releasably seated in the lower jaw 114 of FIG. 6 but can be similarly seated in other types of jaws. The cartridge 132 has a plurality of cut-outs or pockets 148 formed therein, as also shown in FIG. 13, that are similar to the cut-outs 118 of the cartridge 100 of FIG. 6.

The retainer 134 in this illustrated embodiment is in the form of a pan or tray that has a bottom with opposed sidewalls extending upwardly therefrom. The retainer 134 is generally configured and used similar to the retainer 102 of FIG. 6, but the retainer 134 in the illustrated embodiment of FIGS. 11-13 is movably seated in the lower jaw 114. The retainer 134 is configured to move relative to the cartridge 132 and the lower jaw 114 to facilitate release of the adjunct 138. The retainer 134 is configured to move from a locked or engaged configuration, which is shown in FIGS. 11 and 12, to an unlocked or unengaged configuration, which is shown in FIG. 13. In the locked configuration, the retaining elements 136 each releasably engage the adjunct 136, e.g., "lock" the adjunct 136 to the cartridge 132. In the unlocked configuration, the retaining elements 136 are each disengaged from the adjunct 136, e.g., the adjunct 136 is "unlocked" from the cartridge 132.

The retainer 134 includes a release element 150 configured to facilitate movement of the retainer 134 from the locked configuration to the unlocked configuration. The release element 150 is located in a distal portion of the retainer 134 either at the retainer's distal edge or, as in this illustrated embodiment, just proximal to the retainer's distal edge. In this illustrated embodiment, the release element 150 includes a pair of tabs extending upwardly from the retainer's inner bottom surface 134s, although there can be another number of release elements. The release element can have other configurations, such as a semi-spherical protrusion on the retainer's inner bottom surface 134s, a raised elongate bar on the retainer's inner bottom surface 134s, an elongate bar located above the retainer's inner bottom surface 134s and extending between opposed inner sides of the retainer 134, etc.

The release element 150 is configured to engage the sled 144 to move the retainer 134 from the locked configuration to the unlocked configuration. As discussed above, the sled 144 is configured to slide distally along the cartridge 134 and lower jaw 114 on the retainer's inner bottom surface 134s to deploy the staples through the staple cavities 140. The staples pierce through the adjunct 138 as they are deployed, as also discussed above. The sled 144 will contact or abut the release element 150 as its nears the end of its distal translation along the cartridge 134 and lower jaw 114. Continued distal movement of the sled 144 with the sled 144 contacting or abutting the release element 150 pushes the retainer 134 distally relative to the cartridge 134 and lower jaw 114. The retaining elements 136 attached to the retainer 134 will thus also move distally. The distal movement of the retaining elements 136 causes the retaining elements 136 to slide free of the adjunct 138 so as to release the adjunct 138 therefrom. Thus, unlike the embodiments of the retaining elements 104, 124 of FIGS. 6, 9, and 10 that are configured to sequentially release the adjunct coupled thereto in a proximal to distal direction, the retaining elements 136 are configured to simultaneous release the adjunct 138.

As shown in FIGS. 11 and 12, the retaining elements 134 are aligned with the cartridge's cut-outs 148 when the retainer 134 is in the locked configuration. As shown in FIG. 13, the retaining elements 134 are not aligned with the cartridge's cut-outs 148 when the retainer 134 is in the unlocked configuration. The adjunct 136 is thus free to exit the cut-outs 148 when the retainer 134 is in the unlocked configuration.

The cartridge 132 can include open space 152 in a distal portion thereof, as shown in FIG. 12. The retainer 134 is configured to move into the open space 152 when the retainer 134 moves distally to move from the locked configuration to the unlocked configuration.

The cartridge 132 can include a stop element in the distal portion thereof configured to contact or abut the retainer 134 in its locked configuration. The stop element can be configured to stop the distal movement of the retainer 134 relative to the cartridge 132 and lower jaw 114. The stop element can have a variety of configurations, such as one or more tabs extending upwardly from an inner bottom surface of the cartridge 132, a semi-spherical protrusion on the cartridge's inner bottom surface, a raised elongate bar on the cartridge's inner bottom surface, an elongate bar located above the cartridge's inner bottom surface and extending between opposed inner sides of the cartridge 132, etc.

In an exemplary embodiment, the adjunct 138 is releasably coupled to the retaining elements 136 in manufacturing, which may help ensure that the retainer 134 is in a proper location relative to the cartridge 132 prior to staple deployment so the retainer 134 can appropriately slide distally to release the adjunct 138. The adjunct 138 can, however, instead be manually applied to the retaining elements 136 by a user.

In another embodiment, instead of the sled 144 contacting or abutting the release element 150 to push the retainer 134 distally relative to the cartridge 132 and lower jaw 114, an E-beam that advances distally along the cartridge 132 and lower jaw 114 can contact or abut the release element 150 to push the retainer 134 distally relative to the cartridge 132 and lower jaw 114. In yet another embodiment, both the sled 144 and an E-beam can contact or abut the release element 150 to push the retainer 134 distally relative to the cartridge 132 and lower jaw 114.

In another embodiment, instead of the retainer 134 including the release element 150, the cartridge 132 can include the release element 150. The retainer can include an opening for the release element to extend through, e.g., one opening for each of a pair of tabs extending upwardly from the cartridge. The opening and the release element are configured to cooperate to help hold the retainer in position relative to the cartridge until the sled and/or the E-beam contact or abut the release element and push the retainer distally. The release element extending from the cartridge can have elasticity to allow the release element to bend during the distal advancement of the retainer so the retainer can at least partially slide over the release element.

In another embodiment, instead of the sled 144 (and/or the E-beam) contacting or abutting the release element 150 to push the retainer 134 distally relative to the cartridge 132 and lower jaw 114, the sled 144 (and/or the E-beam) contacting or abutting the release element 150 can move the retainer 134 in a downward direction such that the retaining elements 136 move downward and out of engagement with the adjunct 138. The cartridge's bottom surface can slope downward distal to an initial position of the retainer to guide this downward movement of the retainer.

Figure 14:
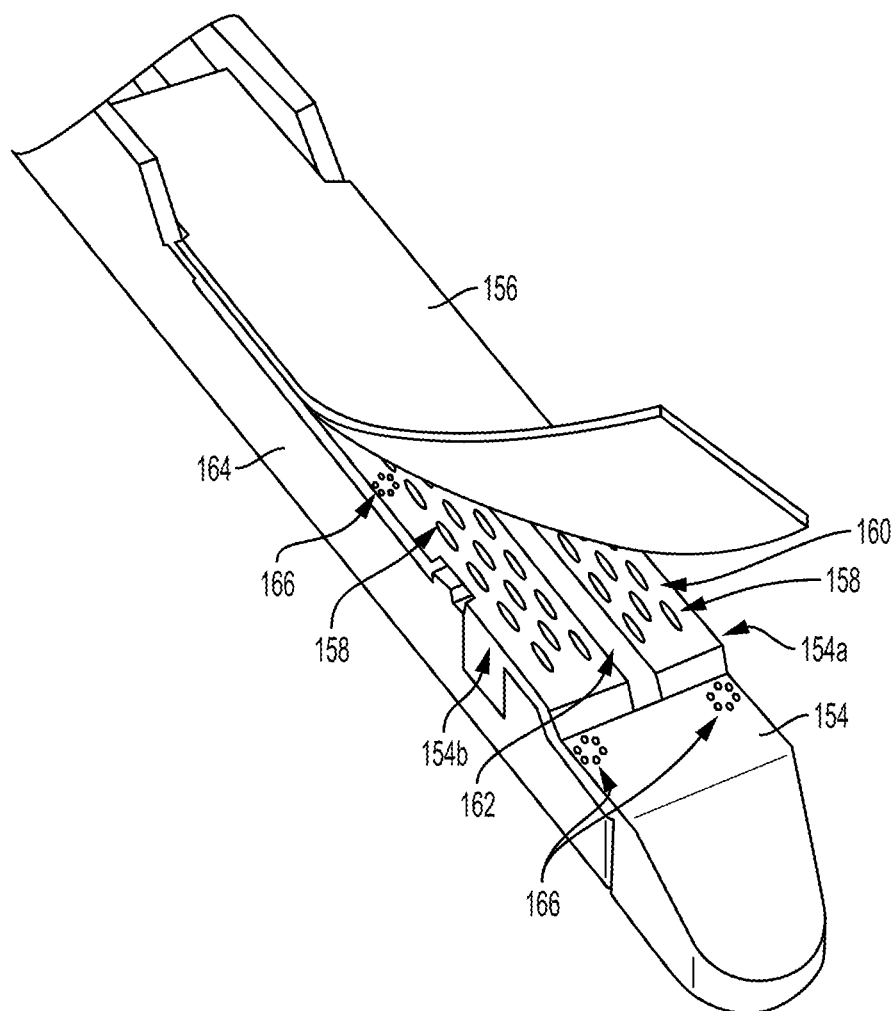
FIG. 14 is a perspective, partial cutaway view of another embodiment of a cartridge having an adjunct releasably retained thereon.

FIG. 14 illustrates another embodiment of a staple cartridge 154 configured to releasably retain an adjunct 156. The staple cartridge 154 is generally configured and used similar to the staple cartridge 40 of FIGS. 1 and 2, e.g., has a plurality of staple cavities 158 in a tissue-facing surface 160 thereof that each seat a staple therein (the staples are obscured in FIG. 14), is configured to have a sled moved therethrough to push the staples out of the staple cavities 158, has a longitudinal slot 162 through which a knife or other cutting element can translate to cut tissue, etc. The staple cartridge 154 is releasably seated in a lower jaw 164 of an end effector that is generally configured and used similar to the lower jaw 114 of FIG. 6.

In this illustrated embodiment, the cartridge 154 includes a plurality of retaining elements 166 configured to releasably retain the adjunct 156 to the cartridge 154. The retaining elements 166 are in the form of pegs, similar to the retaining elements 124 of FIG. 10, that extend upwardly from the tissue-facing surface 160 of the cartridge 154. The retaining elements 166 are arranged in clusters that are longitudinally aligned along opposed sides 154a, 154b of the cartridge 154. The number of retaining elements 166 in each cluster can vary, but in an exemplary embodiment there are at least three retaining elements 166 in each cluster. In an exemplary embodiment there are at least three clusters of retaining elements 166 on each side 154a, 154b of the cartridge 154. For example, one cluster can be near a proximal end of the cartridge 154 for releasable attachment to the adjunct 156 near a proximal end thereof, one cluster can be near a distal end of the cartridge 154 for releasable attachment to the adjunct 156 near a distal end thereof, and one cluster can be near a middle of the cartridge 154 for releasable attachment to the adjunct 156 near a middle thereof. Any additional clusters can be located between the proximal cluster and the middle cluster and/or between the distal cluster and the middle cluster. Regardless of a number of clusters on each side 154a, 154b of the cartridge 154, the clusters can be equidistantly spaced therealong, as in this illustrated embodiment, which may help evenly secure the adjunct 156 to the cartridge 154. In some embodiments, instead of clusters of retaining elements 166, the retaining elements 166 can be individual members aligned longitudinally along the cartridge 154.

The retaining elements 166 are integrally formed with the cartridge 154 in this illustrated embodiment, such as by being molded therewith. In other embodiments, instead of being integral with the cartridge 154, the retaining elements 166 can be separate members attached thereto, such as by welding, adhesive, press fit, etc.

Figure 15:
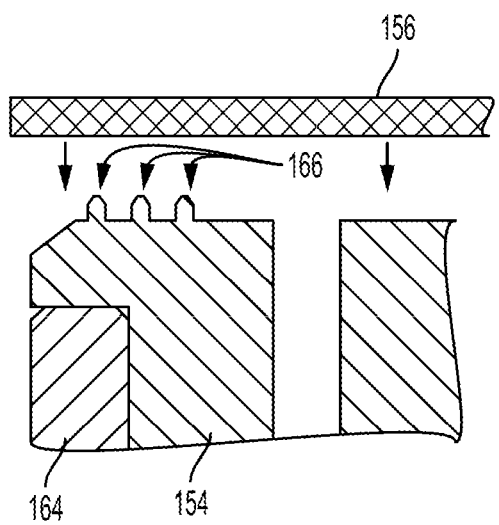
FIG. 15 is a side view of a portion of the cartridge and adjunct of FIG. 14 pre-assembly.
Figure 16:
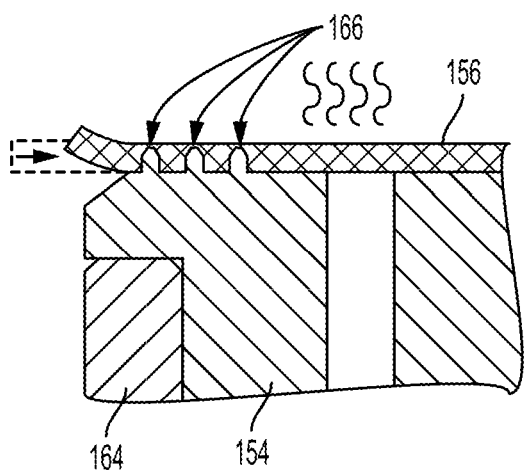
FIG. 16 is a side view of the portion of the assembled cartridge and adjunct of FIG. 15.

The adjunct 156 in this illustrated embodiment is a fibrous structure that is configured to transition from an original, non-contracted configuration to a contracted configuration under application of heat. FIG. 15 illustrates the adjunct 156 in the non-contracted configuration, and FIG. 16 illustrates the adjunct 156 in the contracted configuration. In general, the adjunct 156 can be positioned on the cartridge's tissue-facing surface 160 and heated at least in the areas where the retaining elements 166 are located. The fibers of the adjunct 156 can separate to allow the retaining elements 166 to extend into the adjunct 156. The application of heat to the adjunct 156 is configured to cause the adjunct 156 to transition from the non-contracted configuration to the contracted configuration. The contraction of the adjunct 156 urges the fibers thereof together to grip the retaining features 166 and help hold the adjunct 156 thereto. The contraction of the adjunct 156 can cause the retaining elements 166 to deform, as shown in FIG. 16 in which the retaining elements 166 have become bent from their straight configuration shown in FIG. 15. The deformation of the retaining elements 166 may help grip the adjunct 156 and thereby help hold the adjunct 156 on the cartridge 154 and/or may facilitate release of the adjunct 156 since heating the adjunct 156 can make the adjunct 156 non-flexible. Exemplary embodiments of contractable adjuncts and of releasably coupling the adjunct to a member such as a staple cartridge or anvil are further described in U.S. application Ser. No. 15/435,891 entitled "Methods And Systems For Mating Constrictable Adjunct Materials With End Effectors" filed on even date herewith.

The adjuncts 106, 126, 138, 156 of FIGS. 6, 9-11, and 14 are releasably coupled to a staple cartridge and a lower jaw that seats the staple cartridge. In other embodiments, an adjunct can be releasably coupled to an anvil at an upper jaw of a surgical tool.

Figure 17:
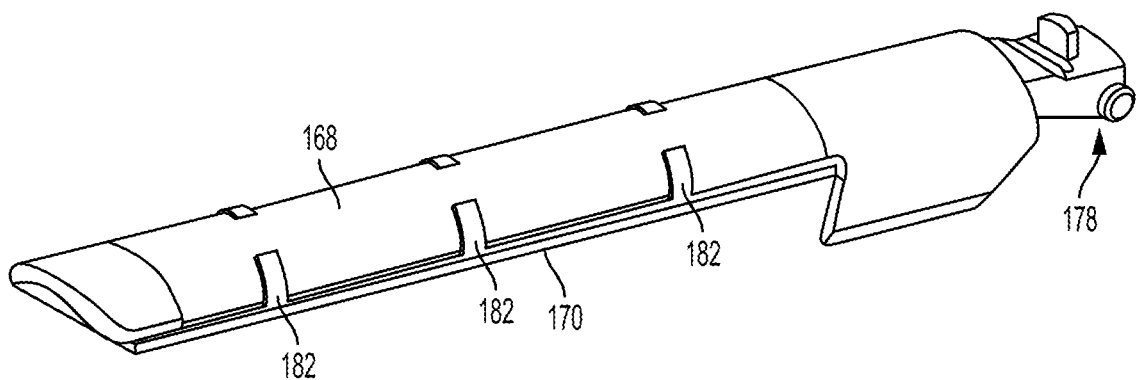
FIG. 17 is a perspective view of an embodiment of an anvil and a retainer coupled thereto.
Figure 18:
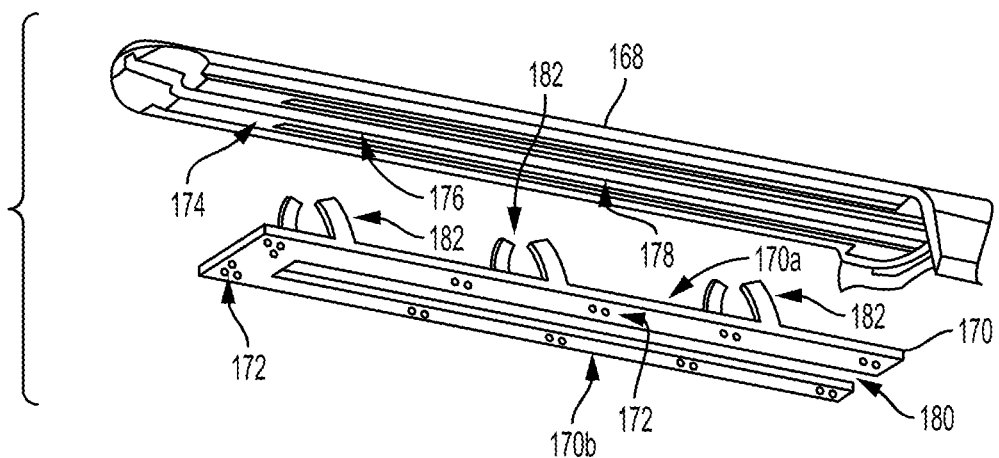
FIG. 18 is an exploded view of the anvil and retainer of FIG. 17.

FIG. 17 illustrates one embodiment of an upper jaw or anvil 168 coupled to a retainer 170 including a plurality of retaining elements 172 configured to releasably retain an adjunct to the anvil 168. FIG. 18 illustrates the anvil 168 and the retainer 170 prior to their coupling. The anvil 168 is generally configured and used similar to the upper jaw 34 of FIGS. 1 and 2, e.g., has a tissue-facing surface 174 with staple forming pockets 176 formed thereon, has a longitudinal slot 178 through which a knife or other cutting element can translate to cut tissue, etc. The anvil 168 includes a coupling mechanism 178 that couples the upper jaw 168 to a lower jaw of the end effector that is configured to cooperate with the upper jaw 168 to engage and staple tissue, as discussed above.

The retainer 170 in this illustrated embodiment is in the form of a plate. The retainer 170 has a longitudinal slot 180 through which a knife or other cutting element can translate to cut tissue, etc. The slot 180 is open at a proximal end thereof to allow the knife or other cutting elements to slide therein. The slot 180 is thus configured to be aligned with the anvil's longitudinal slot 178 when the retainer 170 is coupled to the anvil 168. The slot 180 extends along a partial longitudinal length of the retainer 170 to allow the retainer 170 to be a singular element, e.g., with a connected distal end. In other embodiments, the retainer 170 can be a two-piece element with left and right sides providing a space therebetween through which the knife or other cutting element can translate to cut tissue, etc.

The retainer 170 can be formed from any of a variety of materials. In an exemplary embodiment, the retainer 170 is formed from a plastic or polymer such that the retainer 170 has elasticity.

The retainer 170 is configured to releasably couple to the anvil 168 so as to be positioned over the anvil's tissue-facing surface 174, as shown in FIG. 17. The slot 180 can be wide enough to not obscure any of the staple forming pockets 176 on the anvil's tissue-facing surface 174 such that staples can be deployed from a lower jaw coupled to the upper jaw 168, pierce through the adjunct, and be formed by the staple forming pockets 176.

The retainer 170 includes at least one attachment mechanism 182 configured to releasably attach the retainer 170 to the anvil 168. The retainer 170 being releasably coupled to the anvil 168 may allow for re-use of the retainer 170 with different anvils and/or may facilitate cleaning of the retainer 170 and/or anvil 168 since the retainer 170 can be removed from the anvil 168 prior to cleaning of one or both of the retainer 170 and anvil 168. In other embodiments, the retainer 170 can be fixed to the anvil 168, which may help ensure that the retaining elements 172 are in a desirable location relative to the anvil 168, which may help the adjunct be desirably positioned over the anvil's tissue-facing surface 174. The attachment mechanism 182 in this illustrated embodiment includes a pair of arms. The retainer 170 in this illustrated embodiment including three pairs of arms, but can have another number of pairs in other embodiments. The arms are configured to snap around an exterior of the anvil 168, as shown in FIG. 17.

The attachment mechanism 182 is integrally formed with the retainer 170 in this illustrated embodiment. The attachment mechanism 182 can thus also, in an exemplary embodiment, have elasticity. The attachment mechanism 182 having elasticity may help the attachment mechanism 182 snap around the anvil 168. In other embodiments, instead of being integral with the retainer 170, the attachment mechanism 182 can be a separate member attached thereto.

The retaining elements 172 are in the form of pegs, similar to the retaining elements 124 of FIG. 10, and extend downwardly from the tissue-facing surface 174 of the anvil 168 in a direction toward the lower jaw coupled to the upper jaw 168. The retaining elements 172 are arranged in clusters that are longitudinally aligned along opposed sides 170a, 170b of the retainer 170, similar to the clusters of the retaining elements 166 of FIG. 14 discussed above. Each of the clusters has two retaining elements 172 but can have another number. The retainer 170 has five clusters along each side 170a, 170b of the retainer 170 but can have another number.

Figure 19:
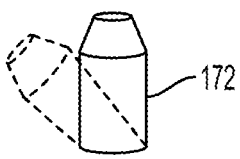
FIG. 19 is a perspective view of a retaining element of the retainer of FIG. 18.

The retaining elements 172 are integrally formed with the retainer 170 in this illustrated embodiment. The retaining elements 172 can thus also, in an exemplary embodiment, have elasticity. FIG. 19 illustrates flexing of the retaining element 172 allowed by the elasticity, with the retaining element 172 in phantom showing the retaining element 172 bent. In other embodiments, instead of being integral with the retainer 170, the retaining elements 172 can be separate members attached thereto. Also, in other embodiments, the retaining elements 172 can be integrally formed with the anvil 168 or be separate members attached thereto such that a retainer is not used.

The adjunct releasably coupled to the anvil 168 can have a variety of configurations, as discussed above. In an exemplary embodiment, the adjunct is a fibrous structure or a film.

Figure 20:
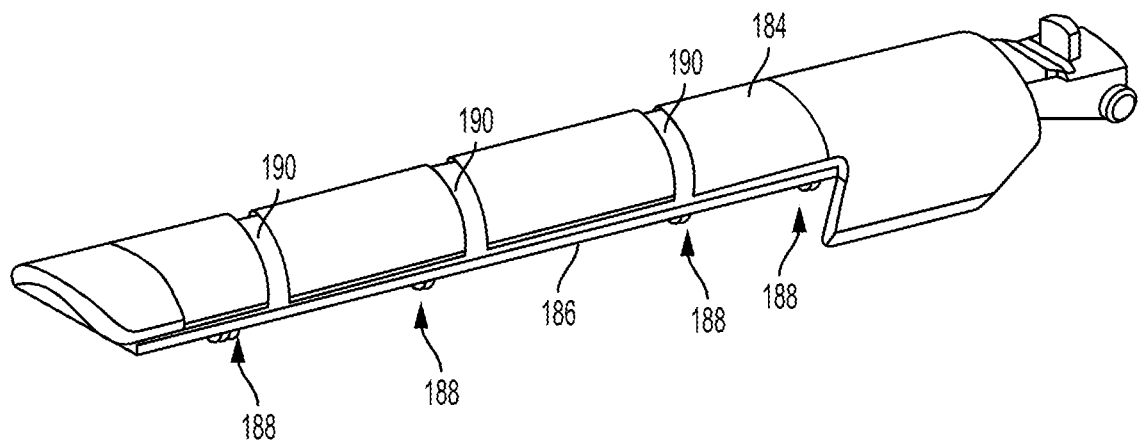
FIG. 20 is a perspective view of another embodiment of an anvil and a retainer coupled thereto.
Figure 21:
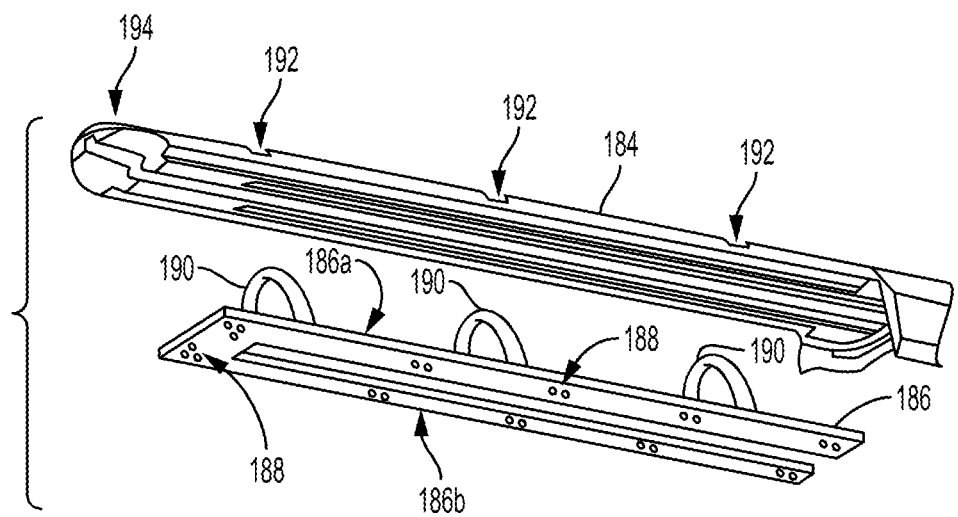
FIG. 21 is an exploded view of the anvil and retainer of FIG. 20.

FIG. 20 illustrates another embodiment of an upper jaw or anvil 184 coupled to a retainer 186 including a plurality of retaining elements 188 configured to releasably retain an adjunct to the anvil 190. FIG. 21 illustrates the anvil 184 and the retainer 186 prior to their coupling. The retaining elements 188 are configured and used similar to the retaining elements 172 of FIG. 18 except that in this illustrated embodiment the proximal-most clusters on either side 186a, 186b of the anvil 184 have three retaining elements 188 each while a remainder of the clusters have two retaining elements 188 each.

The retainer 186 is generally configured and used similar to the retainer 170 of FIG. 18 except that in this illustrated embodiment the retainer's attachment mechanism 190 includes a frame. The retainer 186 in this illustrated embodiment including three frames, but can have another number of frames in other embodiments. The frames are configured to slide around an exterior of the anvil 184 and be seated in recesses 192 formed in the anvil's exterior surface. A distal end 194 of the anvil 184 can be advanced in a distal direction through a proximal-most one of the frames and continue advancing distally until the frames each align with respective ones of the recesses 192, thereby coupling the anvil 184 and the retainer 186 together. The anvil 184 can be moved in a proximal direction relative to the retainer 186 to remove the anvil 184 from the retainer 186. The attachment mechanism 190 can have elasticity, as discussed above, which may facilitate seating thereof in the recesses 190 as well as facilitate removal of the anvil 168 from the retainer 186. The anvil 184 is generally configured and used similar to the anvil 168 of FIG. 18 except that the anvil 184 in this illustrated embodiment includes the recesses 192 that extend radially around its outer surface.

The adjunct releasably coupled to the anvil 184 can have a variety of configurations, as discussed above. In an exemplary embodiment, the adjunct is a fibrous structure or a film.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A staple cartridge assembly for use with a surgical stapler, comprising:
   a cartridge body having a plurality of staple cavities on a tissue-facing surface thereof, each staple cavity having a surgical staple disposed therein; and
   a tray having the cartridge body seated therein and including a plurality of retaining elements on opposed longitudinal sides of the tray extending along opposed longitudinal sides of the cartridge body, the plurality of retaining elements being configured to releasably engage a biocompatible adjunct material such that the adjunct material is disposed on the tissue-facing surface of the cartridge body and is configured to be delivered to tissue by deployment of the surgical staples from the cartridge body and thereby be released from the plurality of retaining elements, wherein the tray is configured to slide longitudinally relative to the cartridge body and thereby allow the release of the adjunct material from the plurality of retaining elements.

2. The staple cartridge assembly of claim 1, wherein the plurality of retaining elements include hooks that are each angled in a same direction.

3. The staple cartridge assembly of claim 1, wherein the plurality of retaining elements include linear pegs extending in a direction substantially perpendicular to the opposed longitudinal sides of the cartridge body.

4. The staple cartridge assembly of claim 1, wherein the tray having the cartridge body seated therein is configured to be releasably seated in a jaw of a surgical stapler.

5. The staple cartridge assembly of claim 1, wherein the adjunct material is made of a plurality of fibers.

6. The staple cartridge assembly of claim 1, wherein the adjunct material is a film, and each of the plurality of retaining elements pierce the film.

7. A staple cartridge assembly for use with a surgical stapler, comprising:
   a cartridge body having a plurality of staple cavities on a tissue-facing, surface thereof, each staple cavity having a surgical staple disposed therein; and
   a tray having the cartridge body seated therein and including a plurality of retaining elements on opposed longitudinal sides of the tray extending along, opposed longitudinal sides of the biocompatible adjunct material such that the adjunct material is disposed on the tissue-facing surface of the cartridge body and is configured to be delivered to tissue by deployment of the surgical staples from the cartridge body and thereby be released from the plurality of retaining elements, wherein the plurality of retaining elements include linear pegs extending in a direction substantially perpendicular to the opposed longitudinal sides of the cartridge body, and wherein each of the linear pegs includes a gripping feature thereon configured to facilitate gripping of the adjunct material.

8. The staple cartridge assembly of claim 7, wherein the tray and the cartridge body are in a fixed position relative to one another.

9. The staple cartridge assembly of claim 7, wherein the tray is configured to slide longitudinally relative to the cartridge body and thereby allow the release of the adjunct material from the plurality of retaining elements.

10. The staple cartridge assembly of claim 7, wherein the plurality of retaining elements include hooks that are each angled in a same direction.

11. The staple cartridge assembly of claim 7, wherein the tray having the cartridge body seated therein is configured to be releasably seated in a jaw of a surgical stapler.

12. The staple cartridge assembly of claim 7, wherein the adjunct material is made of a plurality of fibers.

13. The staple cartridge assembly of claim 7, wherein the adjunct material is a film, and each of the plurality of retaining elements pierce the film.

14. An end effector for a surgical instrument, comprising:
   a first jaw having a cartridge body removably attached thereto, the cartridge body having a plurality of staple cavities configured to seat staples therein that are configured to be deployed from the staple cavities into tissue;
   a second jaw having an anvil with a plurality of staple forming cavities formed on a tissue-facing surface thereof, the first and second jaws being configured to clamp the tissue therebetween; and
   a retainer at one of the first and second jaws, the retainer having a plurality of extensions extending therefrom in a direction toward the other one of the first and second jaws, the plurality of extensions being configured to engage a biocompatible adjunct material to releasably retain the adjunct material to the one of the first and second jaws, and the deployment of the staples being configured to cause the staples to pierce the adjunct material and to cause the adjunct material to be released from the plurality of retaining elements, wherein the retainer is configured to slide longitudinally relative to the cartridge body and thereby allow the release the adjunct material from the plurality of extensions.

15. The end effector of claim 14, wherein the plurality of extensions are arranged longitudinally along each of opposed longitudinal sides of the one of the first and second jaws.

16. The end effector of claim 14, wherein the plurality of extensions include one of a plurality of hooks and a plurality of linear pegs.

17. The end effector of claim 14, wherein the one of the first and second jaws is the first jaw, and the other one of the first and second jaws is the second jaw.

18. The end effector of claim 17, wherein the retainer is a tray seating the cartridge body therein, the tray being seated in a channel of the first jaw.

19. The end effector of claim 14, wherein the one of the first and second jaws is the second jaw, and the other one of the first and second jaws is the first jaw.

20. The end effector of claim 19, wherein the retainer is releasably coupled to the anvil.

* * * * *